(12) United States Patent
Diekmann et al.

(10) Patent No.: US 6,989,549 B2
(45) Date of Patent: Jan. 24, 2006

(54) OPTICAL GAS SENSOR

(75) Inventors: Wilfried Diekmann, Lübeck (DE); Christoph Clausen, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 294 days.

(21) Appl. No.: 10/429,537

(22) Filed: May 5, 2003

(65) Prior Publication Data
US 2004/0007667 A1 Jan. 15, 2004

(30) Foreign Application Priority Data
May 24, 2002 (DE) .................. 102 23 277

(51) Int. Cl.
*G01N 21/00* (2006.01)
*G01N 15/06* (2006.01)

(52) U.S. Cl. .................. 250/573; 356/437; 356/439; 250/343

(58) Field of Classification Search ........... 250/573, 250/574, 343, 339, 341.8, 353; 356/436, 356/437, 438, 439; 73/23.2, 31.05, 863
See application file for complete search history.

(56) References Cited

U.S. PATENT DOCUMENTS

| | | | |
|---|---|---|---|
| 5,163,332 A | 11/1992 | Wong | |
| 5,502,308 A | 3/1996 | Wong | |
| 5,973,326 A | 10/1999 | Parry et al. | |
| 6,469,303 B1 * | 10/2002 | Sun et al. | 250/343 |
| 6,642,522 B2 * | 11/2003 | Clausen et al. | 250/343 |
| 2002/0063216 A1 | 5/2002 | Clausen et al. | |

FOREIGN PATENT DOCUMENTS

| | | |
|---|---|---|
| DE | 40 02 436 | 8/1991 |
| DE | 199 25 196 | 12/2000 |

(Continued)

Primary Examiner—David Porta
Assistant Examiner—Don Williams
(74) Attorney, Agent, or Firm—McGlew & Tuttle, PC

(57) ABSTRACT

A robust gas sensor can be manufactured in a simple manner and at low cost, and have no movable optical components. A measured gas cell (3) has a wall defining a cylindrical space with a measured gas inlet. The measured gas cell (3) is limited in the longitudinal axial direction by a reflective, flat first cover element (1) and by a reflective, flat second cover element (5) arranged at a spaced location from and in parallel to the first cover element (1). The height of the measured gas cell (3) corresponds approximately to 1 to 3 times the diameter of the cover elements (1, 5). The second cover element (5) accommodates a radiation source (6) and two detector elements (23, 24) with at least one measuring detector and one reference detector. The radiation source (6) is arranged displaced by 30% to 60% of the radius of the second cover element (5) from the center of the second cover element (5). Both detector elements (23, 24) are displaced by an amount of 25% to 35% of the radius of the second cover element (5), which amount is equal for both detector elements (23, 24), from a straight line passing through the center of the second cover element (5), wherein the straight line extends at right angles to the diameter of the radiation source (6), and the direction of displacement of the detector elements (23, 24) is opposite that of the radiation source (6). The detector elements (23, 24) are arranged mirror symmetrically to each other and at equal distance from the diameter of the radiation source (6), wherein the distance amounts to 10% to 50% of the radius of the second cover element (5).

21 Claims, 3 Drawing Sheets

FOREIGN PATENT DOCUMENTS

| | | |
|---|---|---|
| DE | 100 58 469 | 5/2002 |
| EP | 0 647 845 A1 | 4/1995 |
| GB | 2 369 884 A | 6/2002 |
| GB | 2 381 579 A | 5/2003 |
| JP | 9-229858 | 9/1997 |
| WO | WO 02/093141 A1 | 11/2002 |

* cited by examiner

OPTICAL GAS SENSOR

FIELD OF THE INVENTION

The present invention pertains to an optical gas sensor based on the concentration-dependent absorption of electromagnetic radiation such as in the infrared wavelength range, through the gas to be measured, i.e., the measured gas.

BACKGROUND OF THE INVENTION

Compact gas analyzers, which make possible low manufacturing costs and a robust design because no movable optical components are used, are made available with such optical gas sensors, as they are disclosed, e.g., in U.S. Pat. No. 5,973,326.

The prior-art principle of measurement of the optical gas sensors is based on the concentration-dependent absorption of electromagnetic radiation, specifically in the infrared wavelength range, through the gas to be measured, i.e., the measured gas. The measured gas, e.g., hydrocarbons, $CO_2$ and other trace gases, diffuses, in general, through a dust protection diaphragm or a flame trap in the form of a fabric or a gas-permeable layer of a sintered or ceramic material into the volume of the cell of the measured gas cell of the gas sensor.

The radiation of at least one broad-band radiation source covering, in general, a larger wavelength range passes through the measured gas cell, and an incandescent lamp or an electrically heated glass or ceramic element is usually used as the radiation source. The radiation leaving the at least one electromagnetic radiation source in a divergent form is focused by means of optically reflective surfaces in order to increase the radiation intensity at the site of the measuring detector and possibly of the reference detector. The signal-to-noise ratio of the gas sensor is increased and the quality of measurement is thus improved by the focusing of the radiation. The detectors used are, in general, pyroelectric crystals, semiconductor elements or so-called thermoelectric piles from thermocouples, which convert the measured radiated power into electric signals, which are evaluated for the determination of the gas concentration to be measured in a suitable manner.

If two or more different measured gases are to be measured with one gas sensor, a number of measuring detectors corresponding to the number of different measured gases are used, which are sensitive to the particular measured gas in a wavelength-specific manner. The selection of the wavelength range or wavelength ranges is performed by means of interference filters, arranged upstream of the corresponding detectors, are directly connected to or combined with the corresponding detectors. A wavelength range contains the wavelength of an absorption band of the measured gas and is detected by the corresponding measuring detector, while the wavelength range detected by the optical reference detector is selected to be such that it is not affected by the absorption of the measured gas. The concentration of the measured gas is determined and the effect of aging effects of the radiation source as well as the effect of possible contaminants in the optical beam path are compensated by forming the quotient and a suitable accounting of the measured signals.

SUMMARY OF THE INVENTION

The object of the present invention is to provide a gas sensor, which makes possible a very compact design without movable optical components and also has improved measuring sensitivity.

According to the invention, an optical gas sensor is provided with a measured gas cell designed as a cylindrical space with a measured gas inlet. The measured gas cell is limited in the longitudinal axial direction by a reflective flat first cover element and by a reflective flat second cover element. The second cover element is arranged at a spaced location from and in parallel to the first cover element. The height of the measured gas cell corresponds approximately to 1 to 3 times the diameter of the cover elements. The second cover element accommodates a radiation source and two detector elements with at least one measuring detector and one reference detector. The radiation source is arranged displaced by 30% to 60% of the radius of the second cover element from the center of the second cover element. Both the detector elements are displaced by an amount of 25% to 35% of the radius of the second cover element, which amount is equal for both detector elements, from a straight line passing through the center of the second cover element. The straight line extends at right angles to the diameter of the radiation source. The direction of displacement of the detector elements is opposite that of the radiation source. The detector elements are arranged mirror symmetrically to each other and at equal distance from the diameter of the radiation source. The distance amounts to 10% to 50% of the radius of the second cover element.

The distance between the detector elements may be 20% to 90% of the radius of the second cover element. The straight line connecting the detector elements extends at right angles to the diameter of the second cover element through the radiation source. The height of the measured gas cell may correspond to 2 to 3 times the diameter of the cover elements.

A temperature sensor may be arranged in the second cover element.

The measured gas cell may be designed in the form of a circular cylinder.

The measured gas cell and/or the cover elements may consist of reflective metallic materials.

Fits (such as recesses, bores or fittings) for receiving the radiation source and the detector elements may be provided in the second cover element. The fits are sealed especially by windows against the measured gas.

The detector elements may be components of a single multiple detector, which is arranged in a detector housing and contains both the measuring detector and the reference detector.

The first cover element may be designed as a measured gas inlet in the form of a fine screen with a residual inner reflective surface of at least 50% of the total inner surface of the first cover element.

Two radiation sources may be used, which assume the position of the detector elements with only one detector element used, which assumes the position of the radiation source.

The three components comprising a radiation source and two detector elements or comprising two radiation sources and one said detector element may form the corners of an equilateral triangle and may be also arranged on a common circle around the center of the second cover element. The circle may have a radius corresponding to 53% of the radius of the second cover element.

An essential advantage of the gas sensor according to the present invention according to claim 1 is that the measured gas cell is designed with a small volume as a cylindrical space with a reflective cell wall and that a first cover element is designed as a flat reflection surface, and a second cover element located opposite in parallel is designed as a likewise flat reflection surface with the indicated geometric arrangement of the radiation source or sources and the detector elements or element in the second cover element, as a result of which the beam paths between the radiation source(s) and the detector(s) are made longer because of multiple reflections with a compact design to increase the measuring sensitivity, and the intensity of the measured signal is increased at the same time at the site of the detectors. In addition, simple manufacture of the gas sensor is possible without complicated adjustments.

In addition, a shorter response time of the gas sensor according to the present invention is achieved due to the compact design.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
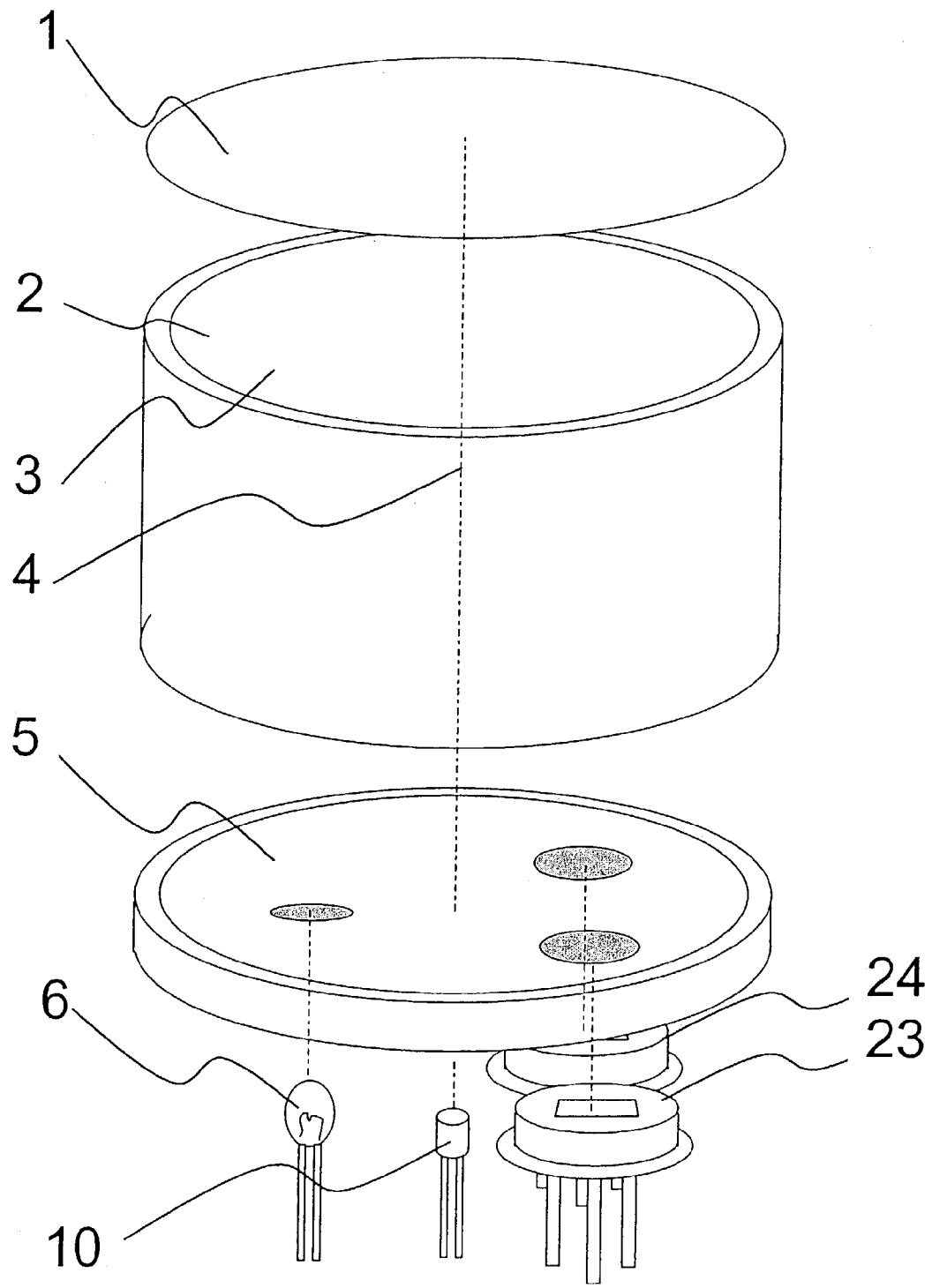
FIG. 1 is an exploded perspective view of a view of a gas sensor.

Referring to the drawings in particular, FIG. 1 shows a view of a gas sensor with the upper first cover element 1 removed and with the lower second cover element 5 lowered.

The use of movable optical components is eliminated in the present invention in order to provide a robust, compact and inexpensive optical gas sensor in a sensor housing. The external dimensions of the circular cylindrical sensor housing according to the exemplary embodiment are only 20 mm in diameter and 30 mm in height, so that it is also possible in particular to build compact, portable gas sensors with the present invention. The radiation source 6 is a broad-band radiator which is known per se. The detector elements 23, 24 have a reference detector and a measuring detector for a certain measured gas. The detectors receive different wavelength ranges of the radiation due to corresponding optical filters arranged upstream. In a special embodiment of the present invention, the detector elements 23, 24 are components of a single multiple detector, which is arranged in the housing and contains both the measuring detector or the measuring detectors corresponding to the number of measured gases and the reference detector.

The specific design of the measured gas cell 3 comprising reflective components according to the present invention leads to a long beam path in a small volume. This is achieved due to the fact that the light propagates by multiple reflections between the flat, upper first cover element 1 and the flat, lower second cover element 5 as well as on the cell wall 2 of the measured gas cell 3. It is essential here, for the highest possible intensity of the measured signal at the site of the detector elements 23, 24, for the radiation source 6 to be arranged displaced by 30% to 60% of the radius of the cover element 5 from the center of the cover element 5 and for both detector elements 23, 24 to be displaced by an equal amount of 25% to 35% of the radius (the distance from center 4 to the wall 2) of the cover element 5 along a straight line passing through the center 4 of the cover element 5. This straight line extends at right angles to the diameter of the second cover element 5 passing through the radiation source 6. The direction of displacement of the detector elements 23, 24 being opposite that of the radiation source 6, see FIG. 2. In addition, the detector elements 23, 24 are mirror symmetrical to each other and are arranged at an equal distance from the diameter of the radiation source 6. The distance amounting to 10% to 50% of the radius of the cover element 5. The displacements are not independent from each other, but are proportionately coupled with one another for the indicated ranges of values.

Figure 2:
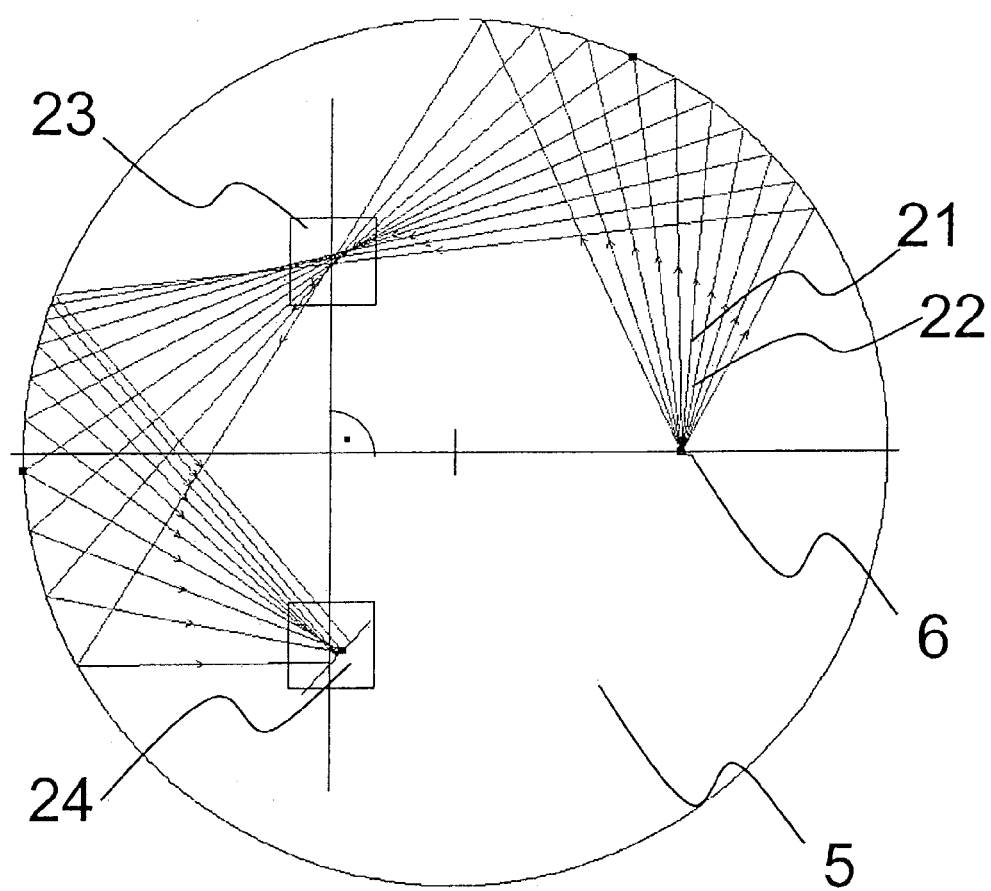
FIG. 2 is a top view of the second cover element showing the optical components and the course of the beams.

An arrangement that is especially favorable with respect to the intensity of the measured signal and the length of the beam paths, is obtained when the radiation source 6 and the detector elements 23, 24 also form the corners of an equilateral triangle and are arranged on a common circle around the center of the cover element 5 with a radius corresponding to 53% of the radius of the cover element 5. This special case is shown in FIG. 2: The two ray beams 21 and 22 sweep, e.g., the same angle range of 60° to 120° in the plane of the cover element 5, but different reflections and beam paths are obtained depending on the angle of radiation in the vertical direction. Thus, there are a large number of ray beams, which reach the detector surfaces. All these ray beams have different angles of radiation. This means that all rays add up at the points at which they reach the surface. As a result, the intensity increases at the measurement positions of the detector elements 23, 24 with every possible course of beam, and the signal intensity of the detectors thus increases. The radiation source 6 and the detector elements 23, 24 are arranged on the second cover element 5, which is used as a bottom plate and is the carrier for the optical components due to corresponding fits being provided in the second cover element 5. The fits may be sealed by means of windows inserted into the second cover element 5 for protecting the detectors and the electric components from moisture and corrosive measured gases. According to FIG. 2, the distance between the detector elements 23, 24 is about 20% to 90% of the radius of the detector element 5 in a preferred embodiment of the present invention, and the straight line shown, which connects the detector elements 23, 24, extends through the radiation source 6 at right angles to the diameter of the cover element 5.

The measured gas is introduced through openings in the first cover element 1. The first cover element 1 may be a fine screen with a residual, effectively reflective inner surface of at least 50%. As an alternative, it has individual holes for admitting the measured gas.

A temperature sensor 10, which is seated especially in a fit, which is drilled from the underside and is not open toward the top side, is advantageously arranged in the lower, second cover element 5 of the gas sensor. Temperature effects in the detector signal can be compensated with the signal of the temperature sensor 10. The cell wall 2 is a circular cylindrical surface, which is located in the beam path and is designed as a reflective surface to improve the signal-to-noise ratio.

If the measured gas is admitted into the measured gas cell 3 preferably via the first cover element 1, it is especially advantageous to use the present invention in portable multiple-gas measuring devices, because a simple possibility of plugging in the gas sensors used and of replacing them in a simple manner is especially important in such a situation. The electric components are located in this situation in the plane of the second cover element 5 located opposite the measured gas inlet, as a result of which the signals can be sent from the device to a lower face in a simple manner.

Compared with the infrared optical gas sensors according to the state of the art, the beam passes several times through the cell volume carrying measured gas within the gas sensor, so that the overall height of the gas sensor and consequently the volume of the cell can be considerably reduced. The measured gas enters the volume of the cell due to diffusion through openings in one of the cover elements 1, 5 or in the cell wall 2. Reduced cell volume leads to a shorter signal response time.

Figure 3:
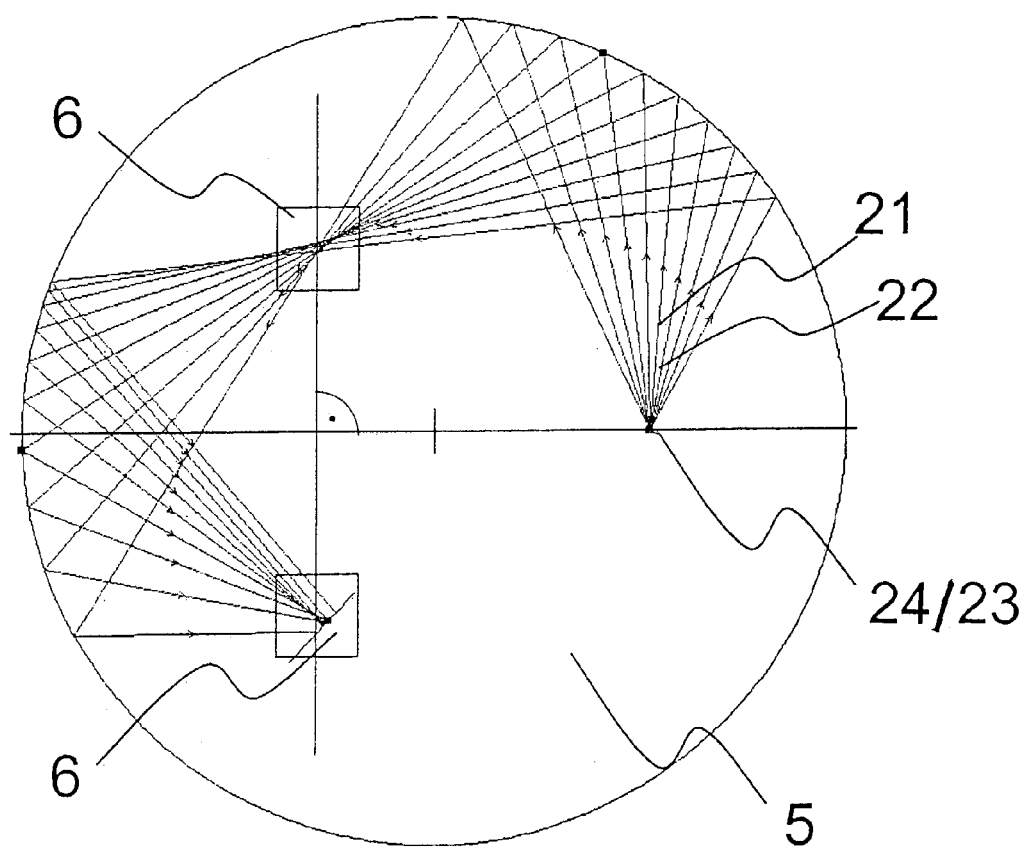
FIG. 3 is a top view of the second cover element showing the optical components and the course of the beams.

According to another possible embodiment of the gas sensor, the positions of the radiation source 6 and the detector elements 23, 24 are transposed such that two radiation sources 6 are used at the positions of the detector elements 23, 24 and one detector is used at the position of the radiation source 6. This is shown schematically in FIG. 3. To select the wavelengths, optical filters are arranged above the fits or fittings, in which the radiation sources 6 are mounted. The drift of the detector is compensated in this case. Effects of aging of the radiation sources 6 are compensated only insofar as the aging process takes place uniformly.

While specific embodiments of the invention have been shown and described in detail to illustrate the application of the principles of the invention, it will be understood that the invention may be embodied otherwise without departing from such principles.

What is claimed is:

1. An optical gas sensor comprising:
   a measured gas cell with a cylindrical part defining a cylindrical space with a measured gas inlet;
   a reflective, flat first cover element;
   a reflective, flat second cover element arranged at a spaced location from and in parallel to the first cover element, said first and second cover element limiting the measured gas cell in a longitudinal axial direction, the height of the measured gas cell corresponding approximately to 1 to 3 times the diameter of the cover elements;
   a radiation source accommodated in said second cover element;
   a measuring detector and one reference detector accommodated in said second cover element, said radiation source being arranged displaced by 30% to 60% of the radius of the second cover element from a center of the second cover element and said detector elements being displaced by an equal amount of 25% to 35% of the radius of the second cover element from a straight line passing through the center of the second cover element, wherein the straight line extends at right angles to the diameter of the radiation source and the direction of displacement of the detector elements is opposite that of the radiation source and the detector elements are arranged mirror symmetrically to each other and at equal distance from the radiation source, wherein the distance amounts to 10% to 50% of the radius of the second cover element.

2. An optical gas sensor in accordance with claim 1, wherein the distance between the detector elements is 20% to 90% of the radius of the second cover element, wherein the straight line connecting the detector elements extends at right angles to the diameter of the second cover element through the radiation source.

3. An optical gas sensor in accordance with claim 1, wherein the height of the measured gas cell corresponds to 2 to 3 times the diameter of the cover elements.

4. An optical gas sensor in accordance with claim 1, further comprising a temperature sensor arranged in said second cover element.

5. An optical gas sensor in accordance with claim 1, wherein the measured gas cell is designed in the form of a circular cylinder.

6. An optical gas sensor in accordance with claim 1, wherein the measured gas cell and/or the cover elements consist of reflective metallic materials.

7. An optical gas sensor in accordance with claim 1, wherein receiving spaces for receiving the radiation source and the detector elements are provided in the second cover element, and the receiving spaces are sealed by windows against the measured gas.

8. An optical gas sensor in accordance with claim 1, wherein the detector elements are components of a single multiple detector, which is arranged in a detector housing and contains both the measuring detector and the reference detector.

9. An optical gas sensor in accordance with claim 1, wherein the first cover element inlet includes a fine screen with a residual inner reflective surface of at least 50% of the total inner surface of the first cover element.

10. An optical gas sensor in accordance with claim 1, wherein two radiation sources are used which assume the position of the detector elements and only one detector element which assumes the position of the radiation source.

11. An optical gas sensor in accordance with claim 1, wherein the three components comprising a radiation source and two said detector elements or comprising two said radiation sources and one detector element form the corners of an equilateral triangle and are also arranged on a common circle around the center of the second cover element, wherein the circle has a radius corresponding to 53% of the radius of the second cover element.

12. An optical gas sensor comprising:
   a measured gas cell with a cylindrical part defining a cylindrical space with a measured gas inlet;
   a reflective, flat first cover element;
   a reflective, flat second cover element arranged at a spaced location from and in parallel to the first cover element, said first and second cover element limiting the measured gas cell in a longitudinal axial direction, the height of the measured gas cell corresponding approximately to 1 to 3 times the diameter of the cover elements;
   a first radiation/detector component accommodated in said second cover element;
   a second radiation/detector component accommodated in said second cover element;
   a third radiation/detector component accommodated in said second cover element, one of said radiation/detector components being arranged displaced by 30% to 60% of a radius of the second cover element from a center of the second cover element and the other of said radiation/detector components being displaced by an equal amount of 25% to 35% of the radius of the second cover element from a straight line passing through the center of the second cover element, wherein the straight line extends at right angles to the diameter of said one of said radiation/detector components and the direction of displacement of the other of said radiation/detector components is opposite that of said one of the radiation/detector components and said other of said radiation/detector components are arranged mirror symmetrically to each other and at equal distance from said one of the radiation/detector components, wherein the distance amounts to 10% to 50% of the radius of the second cover element.

13. An optical gas sensor in accordance with claim 12, wherein said one of said radiation/detector components is a radiation source and said other of said radiation/detector components are each detector elements with a distance between the detector elements from 20% to 90% of the radius of the second cover element, wherein the straight line connecting the detector elements extends at right angles to the diameter of the second cover element through the radiation source.

14. An optical gas sensor in accordance with claim 12, further comprising a temperature sensor arranged in said second cover element.

15. An optical gas sensor in accordance with claim 12, wherein the measured gas cell is designed in the form of a circular cylinder, wherein the height of the measured gas cell corresponds to 2 to 3 times the diameter of the cover elements.

16. An optical gas sensor in accordance with claim 12, wherein the measured gas cell and/or the cover elements consist of reflective metallic materials.

17. An optical gas sensor in accordance with claim 12, wherein said one of said radiation/detector components is a radiation source and said other of said radiation/detector components are each detector elements and receiving spaces for receiving said radiation source and said detector elements are provided in the second cover element, and said receiving spaces are sealed by windows against the measured gas.

18. An optical gas sensor in accordance with claim 12, wherein said one of said radiation/detector components is a radiation source and said other of said radiation/detector components are each detector elements and wherein the detector elements are components of a single multiple detector, which is arranged in a detector housing and contains both the measuring detector and the reference detector.

19. An optical gas sensor in accordance with claim 12, wherein the first cover element inlet includes a fine screen with a residual inner reflective surface of at least 50% of the total inner surface of the first cover element.

20. An optical gas sensor in accordance with claim 12, wherein said one of said radiation/detector components is a detector element and said other of said radiation/detector components are each radiation sources.

21. An optical gas sensor in accordance with claim 12, wherein the three components comprising a radiation source and two said detector elements or comprising two said radiation sources and one detector element form the corners of an equilateral triangle and are also arranged on a common circle around the center of the second cover element, wherein the circle has a radius corresponding to 53% of the radius of the second cover element.

* * * * *